United States Patent
Vanmoor

(12)
(10) Patent No.: US 6,642,272 B1
(45) Date of Patent: Nov. 4, 2003

(54) METHOD OF TREATING A MALE IMPOTENCE CONDITION

(76) Inventor: Arthur Vanmoor, 22 SE. 4 Street, Boca Raton, FL (US) 33432-6016

( * ) Notice: Subject to any disclaimer, the term of this patent is extended or adjusted under 35 U.S.C. 154(b) by 0 days.

(21) Appl. No.: 10/368,219

(22) Filed: Feb. 18, 2003

(51) Int. Cl.⁷ .................. A61K 31/195; A61K 31/19
(52) U.S. Cl. .................. 514/563; 514/561; 514/558
(58) Field of Search .................. 514/563, 561

(56) References Cited

U.S. PATENT DOCUMENTS 6,277,883 B1 * 8/2001 Vanmoor .................. 514/550

* cited by examiner

*Primary Examiner*—Dwayne C. Jones
(74) *Attorney, Agent, or Firm*—Otto S Kauder

(57) ABSTRACT

There is disclosed a method of treating male impotence in a person in need of such treatment, which comprises enhancing the effectiveness of the person's immune system by the administration to such person of an effective amount of at least one water-soluble aminoacid represented by formula (I)

$$X\text{—}C_nH_{2n}\text{—}CR(NH_2)COOH \qquad (I)$$

wherein X represents a hydrogen atom (H) or a carbamoyl group ($CONH_2$), R is hydrogen or a methyl ($CH_3$) group, and n is a whole number from 1 to 4.

14 Claims, No Drawings

METHOD OF TREATING A MALE IMPOTENCE CONDITION

BACKGROUND OF THE INVENTION

1. Field of the Invention

This invention relates to a method of treating a man suffering from an impotence condition with an agent that enhances the effectiveness of the human immune system to mitigate and where possible eliminate the impotence and enhance the man's stamina.

2. Description of Related Art

The human immune system functions to maintain human individuality by fighting off foreign entities. The MERCK MANUAL, 16$_{th}$ edition, published 1992, at pages 279 to 303, which portion is here incorporated by reference, contains a detailed description of the parts of the immune system and of immunodeficiency diseases and hypersensitivity disorders to which it is subject. A table at pages 284–5 titled "Cytokines" lists the major effects of such cytokines or immunoeffective polypeptides as interleukin types, interferon types, alpha- and beta-tumor necrosis factor, three types of colony-stimulating factor, and alpha- and beta-transforming growth factor. A table at page 303 lists disorders with increased susceptibility to unusual infections. Nothing in this publication relates to an impotence condition or remedies therefor.

As is well known, remedies for male impotence and insufficient stamina have been sought for generations by a great variety of methods, and with the increasing application of science some successes have been achieved. However, the search for better remedies for this as well as other suffering conditions is enormously costly. For economic reasons, moreover, the search tends to be skewed in the direction of finding novel remedies proprietary to their discoverers and owners. Novel remedies, of course, come into being with nothing known about either their safety or their effectiveness, so that both of these essential attributes need to be exhaustively studied before they can be used as intended.

In contrast, the art has tended to neglect the exploration of therapeutic properties of known substances that humans have been safely ingesting for untold generations. Along these lines, the present inventor has been able to bring about in susceptible individuals within a limited and reproducible time the appearance of headache, elevated blood pressure, facial pimples, signs of the so-called common cold, and pains in a joint by administering selected foods, food ingredients, and relatively harmless household chemicals as trigger substances, and to use these as research tools to study the effectiveness of certain nutrient substances in relieving these artificially produced conditions as well as their natural counterparts. As a result, certain water soluble amino carboxylic acid compounds are disclosed in U.S. Pat. No. 5,616,617 as effective against facial pimples; certain water soluble amino carboxylic acid compounds are disclosed in U.S. Pat. No. 5,626,831 as effective against the common cold; certain water soluble amino carboxylic acid compounds are disclosed in U.S. Pat. No. 5,707,967 as effective against headache; certain water soluble amino carboxylic acid compounds are disclosed in U.S. Pat. No. 5,708,029 as effective against elevated blood pressure, and certain water soluble amino carboxylic acid compounds are disclosed in U.S. Pat. No. 5,767,157 as effective against pain in a joint.

U.S. Pat. No. 6,277,883 discloses treating male impotence with an aliphatic sulfur compound.

SUMMARY OF THE INVENTION

In accordance with this invention, there is provided a method of treating in a male person in need thereof an impotence condition, which comprises the administration to such person of an amount of a water-soluble aminoacid represented by formula (I) shown below, effective in mitigating that disease.

$$X-C_nH_{2n}-CR(NH_2)COOH \qquad (I)$$

In formula (I), X represents a hydrogen atom (H) or a carbamoyl group (CONH$_2$), R is hydrogen or a methyl (CH$_3$) group, and n is a whole number from 1 to 4. When n is greater than 1, the alkylene group represented by C$_n$H$_{2n}$, can be straight chain or branched.

The effectiveness of the aminoacid represented by formula (I) according to the invention is believed to accompany enhancement of the effectiveness of the person's immune system.

The present invention is based on the recognition that enhancing the effectiveness of the immune system in a person can be beneficial in augmenting the person's innate ability to eliminate toxins from the body and to resist the initiation of the process that leads to a diminished potency as well as to slow down, arrest, and even reverse that process. As a result, the incidence of impotence, premature ejaculation, and psychological discomfort associated with such male sexual dysfunction is diminished, and the quality of life is improved.

In minimizing impotence and other male sexual dysfunction mega-nutrient doses of 2 to 20 grams of a water-soluble aminoacid represented by formula (I) can be administered from one to five times daily, for a total of 2 to 100 grams per day, until monitoring shows sufficient improvement in the user's condition to permit reduction in dose level and ultimately cessation of the treatment. Daily doses of a water-soluble aminoacid represented by formula (I) in the range from 2 to 40 grams per day are preferred. Such doses can be administered in any convenient manner, as by oral administration in any of the usual dosage forms, such as tablets, capsules, solutions, and dispersions in liquid foods such as soups and fruit juices. Alternatively, there can be given sterile solutions of water-soluble aminoacid represented by formula (I) by direct injection into the bloodstream of the person to be treated, as well as by rectal suppositories containing a water-soluble aminoacid represented by formula (I).

In formula (I), when n=1 the alkylene group represented by C$_n$H$_{2n}$ is a methylene group. When n=2, the alkylene group can be ethylene —CH$_2$CH$_2$— or ethylidene —CH(CH$_3$)—, When n=3 and n=4, the alkylene group represented by CnH$_{2n}$ can have each of the known isomeric configurations of such straight chain and branched alkylene groups.

The following table contains preferred water-soluble amino acids represented by formula (I) according to the invention.

| Index | Name | X | R | n |
|---|---|---|---|---|
| 1 | 2-aminobutanoic acid | H | H | 2 |
| 2 | 2-amino-2-methylpropanoic acid | H | CH$_3$ | 1 |
| 3 | 2-amino-3-carbamoylpropanoic acid | CONH$_2$ | H | 1 |
| 4 | 2-amino-4-carbamoylbutanoic acid | CONH$_2$ | H | 2 |
| 5 | 2-amino-3-methylpentanoic acid | H | H | 4 |
| 6 | 2-amino-4-methylpentanoic acid | H | H | 4 |
| 7 | 2-amino-3-methylbutanoic acid | H | H | 3 |

EXAMPLE 1

A 52 year old man with difficulties in maintaining erection and with limited success with the Viagra® brand remedy for impotence was given forty grams of composition comprising several compounds of formula (I) daily spread over the meals of each day and after four weeks of this treatment was achieving normal results, that is results comparable to those the same man achieved at age 30.

What is claimed is:

1. A method of treating a male impotence condition in a person in need of such treatment, which comprises the administration to such person of an effective amount of at least one water-soluble amino acids represented by formula (I)

$$X-C_nH_{2n}-CR(NH_2)COOH \quad (I)$$

wherein X represents a hydrogen atom (H) or a carbamoyl group ($CONH_2$), R is hydrogen or a methyl ($CH_3$) group, and n is a whole number from 1 to 4.

2. The method of claim 1, wherein the aminoacid is administered orally with food.

3. The method of claim 1, wherein the aminoacid is administered by injection into the bloodstream.

4. The method of claim 1, wherein the aminoacid is administered by rectal suppository.

5. The method of claim 1, wherein the effective amount of the aminoacid is administered in one to five daily doses, each dose being in the range of 2 to 20 gram.

6. The method of claim 1, wherein the total of said effective amount of the aminoacid administered daily is in the range of 2 to 100 grams.

7. The method of claim 6, wherein the total of said effective amount of the aminoacid administered daily is in the range of 20 to 50 grams.

8. The method of claim 1, wherein said person experiences relief from the effects of said condition.

9. The method of claim 1 wherein after treatment said condition is not detectable.

10. The method of claim 1 wherein the aminoacid is 2-amino-4-carbamoylbutanoic acid.

11. The method of claim 1 wherein a plurality of water-soluble aminoacids represented by formula (I) is administered.

12. A method of treating a male impotence condition in a person in need of such treatment, which comprises enhancing the effectiveness of the person's immune system by the administration to such person of an effective amount of at least one water-soluble amino acids represented by formula (I)

$$X-C_nH_{2n}-CR(NH_2)COOH \quad (I)$$

wherein X represents a hydrogen atom (H) or a carbamoyl group ($CONH_2$), R is hydrogen or a methyl ($CH_3$) group, and n is a whole number from 1 to 4.

13. The method of claim 12 wherein the aminoacid is 2-amino-4-carbamoylbutanoic acid.

14. The method of claim 12 wherein a plurality of water-soluble aminoacids represented by formula (I) is administered.

* * * * *